(12) United States Patent
Hölscher et al.

(10) Patent No.: US 11,597,895 B2
(45) Date of Patent: Mar. 7, 2023

(54) AROMATIC SUBSTANCE MIXTURES CONTAINING 8,8-DIMETHYL-6,10-DIOXASPIRO[4,5]DECANE

(71) Applicant: SYMRISE AG, Holzminden (DE)

(72) Inventors: Bernd Hölscher, Halle (DE); Marc Mansfeld, Brevörde (DE); Julia Amos, Eschershausen (DE)

(73) Assignee: SYMRISE AG, Holzminden (DE)

( * ) Notice: Subject to any disclaimer, the term of this patent is extended or adjusted under 35 U.S.C. 154(b) by 42 days.

(21) Appl. No.: 16/771,482

(22) PCT Filed: Dec. 14, 2017

(86) PCT No.: PCT/EP2017/082840
§ 371 (c)(1),
(2) Date: Jun. 10, 2020

(87) PCT Pub. No.: WO2019/114969
PCT Pub. Date: Jun. 20, 2019

(65) Prior Publication Data
US 2021/0087500 A1    Mar. 25, 2021

(51) Int. Cl.
*C11D 3/50* (2006.01)
*A61K 8/49* (2006.01)
*A61Q 13/00* (2006.01)
*C11D 3/00* (2006.01)
*C11D 3/20* (2006.01)

(52) U.S. Cl.
CPC ............. *C11D 3/50* (2013.01); *A61K 8/498* (2013.01); *A61Q 13/00* (2013.01); *C11D 3/0068* (2013.01); *C11D 3/2096* (2013.01); *A61K 2800/59* (2013.01)

(58) Field of Classification Search
CPC ........... C11D 3/50; A61K 8/498; A61Q 13/00
See application file for complete search history.

(56) References Cited

U.S. PATENT DOCUMENTS 5,711,952 A    1/1998 Boden et al.
2012/0308486 A1 * 12/2012 Singer ................. A61K 8/4973
424/49

FOREIGN PATENT DOCUMENTS

JP    H11502555 A    3/1999
WO    9630469 A1    10/1996

OTHER PUBLICATIONS

International Search Report and Written Opinion dated Feb. 5, 2018 for corresponding PCT Application No. PCT/EP2017/082840.
Kurt Kulka, "Novel Acetals and Ketals Having the Gem Dimethyl Group," Perfumery and Essential Oil Record, vol. 57, No. 7, 1966, pp. 427-433 XP9503123.
Sell, C.S., "On the Unpredictability of Odor", Angewandte Chemie International Edition, vol. 45, No. 38, 2006, pp. 6254-6261 XP007911257.

* cited by examiner

*Primary Examiner* — Arrie L Reuther
(74) *Attorney, Agent, or Firm* — Polsinelli PC

(57) ABSTRACT

The present invention relates primarily to fragrance substance mixtures, preferably perfume oils, comprising or consisting of (a) 8,8-dimethyl-6,10-dioxaspiro[4,5]decane, i.e. a compound of formula (I) as described herein, and additionally (b) one or more fragrance substance(s) selected from the group consisting of esters, lactones, oximes and sulphur compounds with a molar mass of 240 g/mol or less and/or (c) one or more fragrance substance(s) selected from the group consisting of acetals, ketones and ethers with a molar mass in the range of 126-240 g/mol. The invention further relates to methods for the production of fragrance substance mixtures according to the invention, methods for enhancing the natural freshness and/or radiance and/or for masking or reducing sulphurous, artificial and/or metallic notes of one or more fragrance substances different from the compound of formula (I), perfumed products containing a fragrance substance mixture according to the invention, methods for producing perfumed products according to the invention and the use of the compound of formula (I) for enhancing the natural freshness and/or radiance and/or for masking and/or reducing sulphurous, artificial and/or metallic notes of one or more fragrance substances different from the compound of formula (I).

18 Claims, No Drawings

AROMATIC SUBSTANCE MIXTURES CONTAINING 8,8-DIMETHYL-6,10-DIOXASPIRO[4,5]DECANE

CROSS-REFERENCE TO RELATED APPLICATIONS

This application is a national stage application (under 35 U.S.C. § 371) of PCT/EP2017/082840, filed Dec. 14, 2017, which is incorporated herein by reference in its entirety.

The present invention relates primarily to fragrance substance mixtures, preferably perfume oils, comprising or consisting of (a) 8,8-dimethyl-6,10-dioxaspiro[4,5]decane, i.e. a compound of formula (I) as described herein, and additionally (b) one or more fragrance substance(s), preferably with a fruity olfactory note, selected from the group consisting of esters, lactones, oximes and sulphur compounds with a molar mass of 240 g/mol or less and/or (c) one or more fragrance substance(s) selected from the group consisting of acetals, ketones and ethers with a molar mass in the range of 126-240 g/mol. The invention further relates to methods for the production of fragrance substance mixtures according to the invention, methods for enhancing the natural freshness and/or radiance and/or for masking or reducing sulphurous, artificial and/or metallic notes of one or more fragrance substances different from the compound of formula (I), perfumed products containing a fragrance substance mixture according to the invention, methods for producing perfumed products according to the invention and the use of the compound of formula (I) for enhancing the natural freshness and/or radiance and/or for masking and/or reducing sulphurous, artificial and/or metallic notes of one or more fragrance substances different from the compound of formula (I).

Further aspects and preferred embodiments of the present invention result from the following explanations, the attached examples and in particular the attached patent claims.

The compound of formula (I) (8,8-dimethyl-6,10-dioxaspiro[4.5]decane, CAS Nr.: 702-75-0)

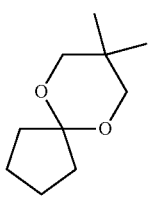
(I)

is known to the skilled person, for example, from the publication Perfumery and Essential Oil Record (1966), 57(7), 427-33, which also reveals an odour description of the compound of formula (I). The odour of the compound of formula (I) is described therein as minty of isopulegol and floral of geranium. In perfumery, however, the compound of formula (I) has so far not been used to any significant extent.

It is also known that the compound of formula (I) can be prepared from cyclopentanone and 2,2-dimethyl-1,3-propanediol, for example, by acetalization:

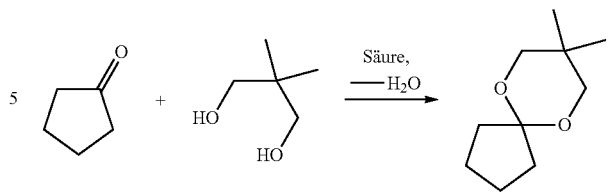

Fruit fragrances in particular play an important role in perfumery and are therefore in great demand in the perfume industry. In addition, there is a constant need to emphasize (accentuate) certain olfactory aspects of a fragrance substance or a fragrance substance mixture; in the case of fruit fragrances, this applies in particular to their natural freshness and radiance. There is also a constant need to mask or reduce certain olfactory aspects of a fragrance substance or a fragrance substance mixture, in particular sulphurous, artificial and metallic notes in the case of fruit fragrance substances.

The primary object was therefore to find (fragrance) substances or (fragrance) substance mixtures which meet the above-mentioned requirements, i.e. which are capable of emphasizing certain pleasant olfactory aspects of a (particularly fruity) fragrance substance/fragrance substance mixture and/or of masking or reducing certain unpleasant olfactory aspects of a (particularly fruity) fragrance substance/fragrance substance mixture.

This object is surprisingly solved by a fragrance substance mixture, preferably a perfume oil, comprising or consisting of the following components:

(a) Compound of formula (I)

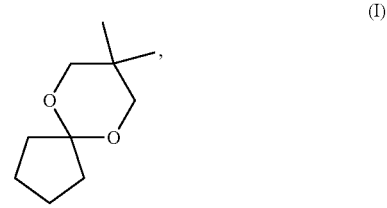
(I)

and additionally (b) one or more fragrance substance(s), preferably with a fruity olfactory note, selected from the group consisting of esters, lactones, oximes and sulphur compounds with a molar mass of 240 g/mol or less and/or (c) one or more fragrance substance(s), selected from the group consisting of acetals, ketones and ethers, with a molar mass in the range of 126-240 g/mol.

Fragrance substance mixtures according to the invention are preferably liquid at 25° C. and 1013 hPa and are usually homogeneous solutions.

According to one embodiment, the fragrance substance mixture according to the invention may comprise or consist of the components (b) and (c) in addition to the component (a). According to a further, alternative embodiment, the fragrance substance mixture according to the invention may comprise or consist of either only component (b) or only component (c) in addition to component (a).

Surprisingly, in a fragrance substance mixture according to the invention, the compound of formula (I) has the effect of emphasizing certain (pleasant) olfactory aspects of the fragrance substance(s) of component (b) and/or the fragrance substance(s) of component (c) and/or of masking or reducing certain (unpleasant) olfactory aspects thereof. In particular, sulphurous, artificial and/or metallic notes of the fragrance substance(s) of components (b) and/or (c) are effectively masked or reduced by the compound of formula (I).

Surprisingly, it has also been shown that the compound of formula (I) has, in addition to its primary sensory properties, additional positive secondary properties, such as high stability under certain conditions of use, preferably in alkaline media (washing powder, fabric softener, soap, shampoo, etc.).

In a fragrance substance composition (e.g. a perfume oil) according to the invention, the person skilled in the art will select the proportion of component (a), i.e. the proportion of the compound of formula (I), in such a way that the desired effect of emphasizing (highlighting) and/or masking or reducing of an olfactory note is achieved, taking care not to use too large an amount of component (a) which could dominate the overall sensory impression of a fragrance substance mixture, and on the other hand not to provide only such a small amount of component (a) that an emphasizing and/or masking/reducing of olfactory aspects of fragrance substances of component (b) or (c) is not or hardly noticeable. For preferred concentration ratios, see the explanations below and the examples attached.

In fragrance substance mixtures according to the invention, the compound of formula (I) is of course used at least in such an amount that a sensory effect is achieved. A sensory effect is achieved by the presence of the compound of formula (I) if a comparative fragrance substance mixture which does not contain a compound of formula (I) with otherwise identical composition is assessed sensorially differently from the fragrance substance mixture according to the invention.

Preferably the compound of formula (I) is used in a fragrance substance mixture according to the invention in such a concentration that the sensory impression of the fragrance substance mixture according to the invention is more natural, fresh, fruity, more radiant, less sulphurous, artificial and metallic than the sensory impression of a comparative fragrance substance mixture which does not contain a compound of formula (I) with otherwise identical composition.

Component (b) of the fragrance substance mixture according to the invention, if present, comprises one or more fragrance substances selected from the group consisting of esters, lactones, oximes and sulphur compounds having a molar mass of 240 g/mol or less. Preferably these fragrance substances have a fruity olfactory note. Such fragrance substances are known to the skilled person; esters, lactones, oximes and sulphur compounds (also those with a fruity olfactory note) represent a very important group of fragrance substances in perfumery.

Surprisingly, the sensory properties of fragrance substances of component (b) are positively influenced by combination with an amount of the compound of formula (I). In individual cases, the sensory impression is preferably shifted in the direction of more natural, fresh, more radiant, less sulphurous, artificial and metallic, although other sensory influences can of course also be observed in individual cases. Detailed descriptions of odours can be found in the attached examples.

The fragrance substances of component (c), if present, regularly function as base notes of a fragrance substances mixture according to the invention or a perfume oil according to the invention. The fragrance substances of component (c) of the fragrance substance mixture according to the invention are acetals, ketones and ethers, with a molar mass in the range of 126-240 g/mol.

If certain fragrance substances contained in the fragrance substance mixture according to the invention have several functional groups, so that they exceptionally fall under component (b) and component (c) at the same time, these are preferably assigned—in particular for the purpose of determining the preferred amounts or mass ratios described herein—50% by weight to component (b) and 50% by weight to component (c), unless indicated otherwise in individual cases.

Fragrance substance mixtures according to the invention, in particular perfume oils according to the invention, can be used in liquid form, undiluted or diluted with a solvent for perfuming or aromatizing. Suitable solvents for this purpose are in particular ethanol, glycerol, 1,2-propylene glycol, 1,2-butylene glycol, dipropylene glycol, diethyl phthalate, triethyl citrate, isopropyl myristate and triacetin.

Ethers and esters having a molar mass of 240 g/mol or less are not counted as components (b) or (c) provided that they are a compound selected from the group consisting of dipropylene glycol, diethyl phthalate and triacetin.

Preferably fragrance substance mixtures according to the invention, preferably perfume oils according to the invention, are combined with further components. Preferred further components are selected from the group consisting of:

Preservatives, preferably those mentioned in US 2006/0089413, abrasives, anti-acne agents and agents for sebum reduction, preferably those mentioned in WO 2008/046791, agents against skin aging, preferably those mentioned in WO 2005/123101, antibacterial agents, anti-cellulite agents, anti-dandruff agents, preferably those mentioned in WO 2008/046795, anti-inflammatory agents, irritation-preventing agents, anti-irritants (anti-inflammatory, irritation-inhibiting and irritation-preventing agents), preferably those mentioned in WO 2007/042472 and US 2006/0089413, antimicrobial agents, preferably those mentioned in WO 2005/123101, antioxidants, preferably those mentioned in WO 2005/123101, astringents, antiseptic agents, antistatic agents, binders, buffers, carrier materials, preferably those mentioned in WO 2005/123101, chelate formers, preferably those mentioned in WO 2005/123101, cell stimulants, cleansing agents, caring agents, depilatories, surface-active substances, deodorants and antiperspirants, preferably those mentioned in WO 2005/123101, plasticizers, emulsifiers, preferably those mentioned in WO 2005/123101, enzymes, essential oils, preferably those mentioned in US 2008/0070825, insect repellents, preferably those mentioned in WO 2005/123101, fibers, film formers, fixatives, foaming agents, foam stabilizers, foam inhibitors, foam boosters, fungicides, gelling agents and gel-forming agents, preferably those mentioned in WO 2005/123101, hair care agents, hair shaping agents, hair straightening agents, moisture regulators (moisturising, moistening and/or moisture-retaining substances), preferably those mentioned in WO 2005/123101, osmolytes, preferably those mentioned in WO 2005/123101, compatible solutes, preferably those mentioned in WO 01/76572 and WO 02/15686, bleaching agents, strengthening agents, stain-removing agents, optical brightening agents, impregnating agents, dirt-repellent agents, friction reducing agents, lubricants, moisturising creams, ointments, opacifiers, plasticising agents, covering agents, polish, glazing agent, polymers, preferably those mentioned in WO 2008/046676, powders, proteins and protein hydrolysates, preferably those mentioned in WO 2005/123101 and WO 2008/046676, refatting agents, abrasive agents, skin soothing agents, skin cleansing agents, skin care agents, skin repair agents, preferably containing cholesterol and/or fatty acids and/or ceramides and/or pseudoceramides, thereby preferably those mentioned in WO 2006/053912, skin lightening agents, preferably those mentioned in WO 2007/110415, skin protecting agents, skin softening agents, skin cooling agents, preferably those mentioned in WO 2005/123101, skin warming agents, preferably those mentioned in WO 2005/123101, stabilizers, UV absorbing agents and UV filters, preferably those mentioned in WO 2005/123101, benzylidene beta-dicarbonyl compounds, preferably those mentioned in WO 2005/107692, alpha-benzoyl cinnamic acid nitriles, preferably those mentioned in WO 2006/015954, AhR receptor antagonists, preferably those mentioned in WO 2007/128723 and WO 2007/060256, detergents, fabric softeners, suspending agents, skin tanning agents, preferably those mentioned in WO 2006/045760, thickening agents, vitamins, preferably those mentioned in WO 2005/123101, oils, waxes and fats, preferably those mentioned in WO 2005/123101, phospholipids, preferably those mentioned in WO 2005/123101, fatty acids (saturated fatty acids, mono- or polyunsaturated fatty acids, α-hydroxy acids, polyhydroxy fatty acids), preferably those mentioned in WO 2005/123101, liquefiers, dyes and colour-protecting agents as well as pigments, preferably those mentioned in WO 2005/123101, anti-corrosives, aroma and flavour substances as well as further additional fragrance substances, preferably those listed in S. Arctander, Perfume and Flavor Chemicals, self-published, Montclair, N.J., 1969 and Surburg, Panten, Common Fragrance and Flavor Materials, 5th Edition, Wiley-VCH, Weinheim 2006, in particular the further fragrance substances explicitly mentioned in US 2008/0070825, which are not already part of the components (b) or (c) of a fragrance substance mixture according to the invention or of a perfume oil according to the invention, alcohols and polyols, preferably those mentioned in WO 2005/123101, surfactants, preferably those mentioned in WO 2005/123101, animal extracts, yeast extracts, extracts of algae or microalgae, electrolytes, liquefiers, organic solvents, preferably those mentioned in WO 2005/123101, or silicones and silicone derivatives, preferably those mentioned in WO 2008/046676.

However, compounds which fall under the definition of components (b) and/or (c) are assigned to these components regardless of their intended use; for exceptions for certain solvents see above.

Furthermore, fragrance substance mixtures according to the invention, in particular perfume oils according to the invention, may be adsorbed on a carrier which ensures both a fine distribution of the fragrance substances contained therein in the product and a controlled release during use. Such carriers may be porous inorganic materials such as light sulphate, silica gels, zeolites, gypsum, clays, clay granules, aerated concrete, etc. or organic materials such as woods, cellulose-based materials, sugars, dextrins (e.g. maltodextrin) or plastics such as PVC, polyvinyl acetates or polyurethanes.

Fragrance substance mixtures according to the invention, in particular perfume oils according to the invention, can also be present microencapsulated, spray-dried, as inclusion complexes or as extrusion products and can be added in this form e.g. to a perfumed product (as described further below).

If necessary, the properties of the compositions modified in this way can be further optimised by so-called "coating" with suitable materials with a view to more targeted fragrance release, preferably using waxy plastics such as e.g. polyvinyl alcohol.

The microencapsulation of the fragrance substance mixtures according to the invention, preferably of the perfume oils according to the invention, can be carried out, for example, by the so-called coacervation process using capsule materials, e.g. made of polyurethane-like substances or soft gelatine. The spray-dried fragrance substance compositions can be produced, for example, by spray-drying an emulsion or dispersion containing the fragrance substance mixture according to the invention, preferably a perfume oil, whereby modified starches, proteins, dextrin and vegetable gums can be used as carriers. Inclusion complexes can be prepared, for example, by incorporating dispersions of the fragrance substance mixture according to the invention, preferably a perfume oil according to the invention, and cyclodextrins or urea derivatives in a suitable solvent, e.g. water. Extrusion products can be obtained by fusing a fragrance substance mixture according to the invention, preferably a perfume oil according to the invention, with a suitable waxy substance and by extrusion with subsequent solidification, if necessary in a suitable solvent, e.g. isopropanol.

A fragrance substance mixture according to the invention as described herein, wherein component (b) comprises two, three, four, five or more different fragrance substances and/or component (c) comprises two, three, four, five or more different fragrance substances, is preferred.

Particularly preferred is a fragrance substance mixture according to the invention as described herein, wherein the mass ratio of the total amount of fragrance substance(s) of component (b), if present, to the compound of formula (I) is greater than or equal to 40:60, preferably greater than or equal to 80:20, more preferably greater than or equal to 99:1, and/or the mass ratio of the total amount of fragrance substance(s) of component (c), if present, to the compound of formula (I) is greater than or equal to 60:40, preferably greater than or equal to 80:20, more preferably greater than or equal to 90:10.

Our own investigations have shown that these mass ratios are particularly advantageous. At these mass ratios, the intrinsic odour of the compound of formula (I) is regularly no longer or hardly perceptible, but the presence of the compound of formula (I) has a positive effect on the overall note of the fragrance substance mixture according to the invention. It is particularly surprising that the compound of formula (I), even in low concentrations, has an effect on the freshness and radiance of the fragrance substance mixture according to the invention, without itself producing or emphasizing a fruity odour to any relevant degree.

Furthermore, a fragrance substance mixture according to the invention as described herein is particularly preferred, wherein the, one, several or all fragrance substance(s) of component (b), if present, has/have a molar mass in the range of 130 to 240 g/mol.

Preferred is also a fragrance substance mixture according to the invention as described herein, wherein the, one, several or all of the fragrance substance(s) of component (b), if present, is/are selected are selected from the group consisting of allyl capronate, allylcyclohexyl propionate, 5-hexyl-4-methyl-tetrahydrofuran-2-one, ethyl-2-cyclopent-2-en-1-yl acetate, 1-cyclohexylethyl-(E/Z)-but-2-enoate, 1,5-dimethylbicyclo[3.2.1]octan-8-one oxime, 2,4,6-trimethyl-4-phenyl-1,3-dioxane, 2-methyl-4-propyl-1,3-oxathiane, isopentyl acetate, ethyl-2-(2,4-dimethyl-1,3-dioxolan-2-yl)acetate, ethyl-2-methyl butanoate, (2-cyclopentylcyclopentyl)-(E/Z)-but-2-enoate, 4-methoxy-2-methyl-butane-2-thiol, 1,3-di methylbutyl-(E/Z)-but-2-enoate, 1,3-dimethylbut-3-enyl-2-methylpropanoate, 1-methoxyhexane-3-thiol, 4-isopropyl-1-methyl-7-thiabicyclo[2.2.1]heptane, 2-(4-methylcyclohex-3-en-1-yl)propane-2-thiol, 5-methyl-2-(1-methyl-1-sulfanyl-ethyl)cyclohexanone, (1,3-di methyl-3-phenyl-butyl)acetate, allyl-2-isopentyloxyacetate, 5-butyltetrahydrofuran-2-one, 5-pentyltetrahydrofuran-2-one, 5-heptyltetrahydrofuran-2-one, 5-octyltetrahydrofuran-2-one, 5-hexyltetrahydrofuran-2-one, ethyl-2-(2-methyl-1,3-dioxolan-2-yl)acetate and diethylcyclohexan-1,4-dicarboxylate, and/or the, one, several or all of the fragrance substance(s) of component (c), if present, is/are selected are selected from the group consisting of 1-(2,6,6-trimethylcyclohex-2-en-1-yl)hepta-1,6-dien-3-one, 1-(2,6,6-trimethylcyclohex-2-en-1-yl)but-2-en-1-one, 1-(2,6,6-trimethylcyclohexen-1-yl)but-2-en-1-one, 1-(2,6,6-trimethylcyclohex-3-en-1-yl)but-2-en-1-one, 1-(2,4,4-trimethylcyclohex-2-en-1-yl)but-2-en-1-one, 1-methyl-4-(2,2,3-trimethylcyclopent-3-en-1-yl)-2-oxabicyclo[2.2.2]octane, 4-(4-methoxyphenyl)-butan-2-one, 5-methylhept-2-en-4-one, 6,6-dimethoxy-2,5,5-trimethyl-hex-2-ene and 2,4,6-trimethyl-4-phenyl-1,3-dioxane.

Fragrance substance mixtures according to the invention, preferably perfume oils according to the invention, are particularly preferred, wherein the, one, several or all of the fragrance substance(s) of component (b), is/are selected are selected from the group consisting of allyl capronate, allylcyclohexyl propionate, 5-hexyl-4-methyl-tetrahydrofuran-2-one, ethyl-2-cyclopent-2-en-1-yl acetate, 1-cyclohexylethyl-(E/Z)-but-2-enoate, 1,5-dimethylbicyclo[3.2.1]octan-8-one oxime, 2-methyl-4-propyl-1,3-oxathiane, isopentyl acetate, ethyl-2-(2,4-dimethyl-1,3-dioxolan-2-yl)acetate, ethyl-2-methylbutanoate, (2-cyclopentylcyclopentyl)-(E/Z)-but-2-enoate, 4-methoxy-2-methyl-butane-2-thiol, 1-methoxyhexane-3-thiol, 4-isopropyl-1-methyl-7-thiabicyclo[2.2.1]heptane, 2-(4-methylcyclohex-3-en-1-yl)propane-2-thiol.

Particularly preferred are fragrance substance mixtures according to the invention, preferably perfume oils according to the invention, as described herein, in which the component (b) is an ester or a sulphur compound.

Further examples of fragrance substances which may be part of component (c) are known to the person skilled in the art and can be found for example in S. Arctander, Perfume and Flavor Materials, Vol. I and II, Montclair, N.J., 1969, self-published or H. Surburg, J. Panten, "Common Fragrance and Flavor Materials", 5$^{th}$ ed., Wiley-VCH, Weinheim 2006.

A further aspect of the present invention relates to a method for the production of a fragrance substance mixture according to the invention, preferably of a perfume oil, as described herein, comprising or consisting of the following step:

Mixing component (a) as defined herein with component (b) and/or (c) as defined herein.

A method as described herein, resulting in a fragrance substance mixture according to the invention (as described herein), preferably a perfume oil, is preferred, in which the mass ratio of the total amount of fragrance substance(s) of component (b), if present, to the compound of formula (I) is greater than or equal to 40:60, preferably greater than or equal to 80:20, more preferably greater than or equal to 99:1, and/or the mass ratio of the total amount of fragrance substance(s) of component (c), if present, to the compound of formula (I) is greater than or equal to 60:40, preferably greater than or equal to 80:20, more preferably greater than or equal to 90:10.

Another aspect of the present invention relates to a method for enhancing the natural freshness and/or radiance and/or for masking or reducing sulphurous, artificial and/or metallic notes of one or more fragrance substances different from the compound of formula (I), preferably of one or more fragrance substances different from the compound of formula (I) having a fruity olfactory note, comprising the following step:

Mixing the fragrance substances different from the compound of formula (I) with an amount of compound of formula (I) sufficient to enhance the natural freshness and/or radiance of the fragrance substances different from the compound of formula (I) and/or to mask or reduce sulphurous, artificial and/or metallic notes of the fragrance substances different from the compound of formula (I).

Particularly preferred is a method as described herein, wherein the, one, several or all of the fragrance substance(s) different from the compound of formula (I) is/are selected from the components (b) and/or (c) of a fragrance substance mixture according to the invention (as described herein).

Further preferred is a method as described herein, wherein the mass ratio of the total amount of fragrance substance(s) of component (b), if present, to the compound of formula (I) is greater than or equal to 40:60, preferably greater than or equal to 80:20, more preferably greater than or equal to 99:1, and/or the mass ratio of the total amount of fragrance substance(s) of component (c), if present, to the compound of formula (I) is greater than or equal to 60:40, preferably greater than or equal to 80:20, more preferably greater than or equal to 90:10.

The above statements on (preferred) fragrance substance mixtures according to the invention apply accordingly to the methods according to the invention.

Another aspect of the present invention relates to a perfumed product containing a fragrance substance mixture according to the invention, preferably a perfume oil, as described herein, preferably in a sensorially effective amount.

"Sensorially effective amount" means in the present context that the perfumed product according to the invention reveals the sensory properties of the fragrance substance mixture according to the invention during operation or use.

Preferred perfumed products according to the invention are selected from the group consisting of perfume extracts, eau de parfums, eau de toilettes, aftershaves, eau de colognes, pre-shave products, splash colognes, perfumed refreshing cloths, acidic, alkaline and neutral detergents, textile fresheners, ironing aids, liquid detergents, powdered detergents, laundry pre-treatment agents, fabric softeners, washing soaps, washing tablets, disinfectants, surface disinfectants, air fresheners, aerosol sprays, waxes and polishes, personal care products, hand creams and lotions, foot creams and lotions, depilatory creams and lotions, aftershave creams and lotions, tanning creams and lotions, hair care products, deodorants and antiperspirants, decorative cosmetic products, candles, lamp oils, incense sticks, insecticides, repellents and fuels.

Particularly preferred perfumed products according to the invention are selected from the following list:
- eau de parfums, eau de toilettes, aftershaves, eau de colognes, pre-shave products, splash-colognes;
- acidic, alkaline and neutral detergents, particularly in the household sector, preferably floor cleaners, window glass cleaners, dishwashing agents, bath and sanitary cleaners, scouring milk, solid and liquid toilet cleaners, powder and foam carpet cleaners, liquid detergents, powder detergents, fabric softeners, surface disinfectants, particularly for hard surfaces (hard surface cleaners);
- personal care products, preferably solid and liquid soaps, shower gels, shampoos, shaving soaps, shaving foams;
- cosmetic emulsions of the oil-in-water, water-in-oil and water-in-oil-in-water type, preferably skin creams and lotions, face creams and lotions, sun protection creams and lotions, after-sun creams and lotions, hand creams and lotions, foot creams and lotions, depilatory creams and lotions, aftershave creams and lotions, skin tanning creams and lotions, skin whitening creams and lotions;
- hair care products, preferably hair sprays, hair gels, firming hair lotions, hair conditioners, permanent and semi-permanent hair dyes, hair tonics, hair creams and lotions;
- deodorants and antiperspirants, preferably underarm sprays, roll-ons (preferably as alcoholic or non-alcoholic solution, as gel or (micro)emulsion, deodorant sticks, deodorant creams.

Particularly preferred perfumed products according to the invention are detergents and cleaning agents, hygiene or care products, especially in the field of body and hair care, cosmetics and household.

Furthermore, preferred perfumed products according to the invention are those wherein the proportion of the fragrance substance mixture according to the invention in the perfumed product is 0.01 to 10% by weight, preferably 0.1 to 5% by weight, particularly preferably 0.25 to 3% by weight, based on the total mass of the perfumed product, respectively.

Moreover, the invention relates to a method for producing a perfumed product, preferably a perfumed product according to the invention (as described herein), comprising or consisting of the following steps:
i) Providing a fragrance substance mixture according to the invention or producing a fragrance substance mixture according to a method according to the invention,
ii) providing the further components of the perfumed product, and
iii) contacting the further components of the perfumed product provided in step ii) with a sensorially effective amount of the fragrance substance mixture provided in step i), preferably wherein the amount of the compound of formula (I) is sufficient to enhance the natural freshness and/or radiance of the, one, several or all fragrance substances of components (b) and/or (c) and/or to mask or reduce sulphurous, artificial and/or metallic notes of the, one, several or all fragrance substances of components (b) and/or (c),
or
I) providing the components of the perfumed product which are not components (a), (b) or (c) of a fragrance substance mixture according to the invention (as described herein),
II) mixing the components of the perfumed product provided in step I) with components (b) and/or (c) of a fragrance substance mixture according to the invention, so as to result in a mixture in which the total amount of components (b) and/or (c) is present in a sensorially effective amount,
III) contacting the mixture prepared in step II) with an amount of the compound of formula (I), preferably wherein the amount of the compound of formula (I) is sufficient to enhance the natural freshness and/or radiance of the, one, several or all fragrance substances of components (b) and/or (c) and/or to mask or reduce sulphurous, artificial and/or metallic notes of the, one, several or all fragrance substances of components (b) and/or (c).

Finally, the invention also relates the use of the compound of formula (I)

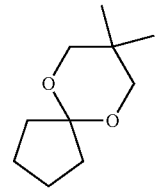

(I)

for enhancing the natural freshness and/or radiance and/or for masking or reducing sulphurous, artificial and/or metallic notes of one or more fragrance substances different from the compound of formula (I), preferably of fragrance substances with a fruity olfactory note.

Preferred is a use of the compound of formula (I) according to the invention, wherein the, one, several or all of the fragrance substance(s) different from the compound of formula (I) is/are selected from the components (b) and/or (c) of a fragrance substance mixture according to the invention.

What has been said above in connection with fragrance substance mixtures according to the invention applies accordingly to the (preferred) embodiments of the methods, perfumed products and uses according to the invention as described herein.

Furthermore, what is said within the scope of an embodiment of the present invention described herein naturally also applies to other embodiments described herein. Accordingly, the embodiments described herein may be combined with each other in any way—as far as it makes sense for the skilled person.

The following examples explain the invention. Unless otherwise stated, proportions and percentages refer to the weight.

Abbreviations Used

Dipropylene glycol (DPG), Diethyl phthalate (DEP), triethyl citrate (TEC), isopropyl myristate (IPM); nat.=natal;

For explanations of the product names of fragrance substances see e.g. S. Arctander, Perfume and Flavor Materials, Vol. I and II, Montclair, N.J., 1969, self-published or H. Surburg, J. Panten, "Common Fragrance and Flavor Materials", 5th ed., Wiley-VCH, Weinheim 2006.

EXAMPLES

1. Example: Perfume Oil P1

| | |
|---|---|
| ETHYL ACETOACETATE | 3 |
| ALDEHYDE C14 SO CALLED 10% DPG | 4 |
| ALLYLAMYL GLYCOLATE | 3 |
| ALLYLCYCLOHEXYL PROPIONATE | 2 |
| ALLYL HEPTYLATE 10% DPG | 3 |
| ALLYL IONONE | 1.5 |
| AMBRETTOLIDE | 2 |
| AMBRINOL S 10% DPG | 1 |
| AMBROXIDE | 1 |
| BENZALDEHYDE DD 10% DPG | 1 |
| BENZYL ACETATE | 5 |
| BENZYL ISOBUTYRATE | 0.5 |
| BENZYL SALICYLATE | 20 |
| BOURGEONAL | 1 |
| CALONE 10% DPG | 8 |
| CARYOPHYLLENE NAT. RECT. | 8 |
| CITRONELLOL 950 | 3 |
| CITRONELLYL ISOBUTYRATE | 3 |
| CYCLAMEN ALDEHYDE | 12 |
| Lemon IDENTOIL ® | 30 |
| DAMASCONE ALPHA 10% DPG | 3 |
| DECALACTONE GAMMA | 1 |
| DIHYDROMYRCENOL | 20 |
| DIMETHYL BENZYL CARBINYL BUTYRATE | 4 |
| DIPROPYLENE GLYCOL | 18.5 |
| DUPICAL 10% DPG | 1 |
| ETHYL BUTYRATE 1% DPG | 5 |
| ETHYL METHYL BUTYRATE-2 10% DPG | 2 |
| EVERNYL 10% DPG | 5 |
| FLORAZON | 1 |
| FLORHYDRAL 10% DPG | 3 |
| FLOROSA | 40 |
| GALAXOLIDE TYPE BASE NEW | 100 |
| GERANIOL SUPRA | 6 |
| GERANYL ACETATE PURE | 5 |
| GLOBALIDE ® | 10 |
| GRAPEFRUIT PHASE C | 20 |
| HEDIONE | 130 |
| HELIONAL | 20 |
| HELIOTROPIN/PIPERONAL 10% DPG | 2 |
| HEXENOL CIS-3 | 1 |
| HEXENYL ACETATE CIS-3 10% DPG | 7 |
| HEXENYL BENZOATE CIS-3 | 1 |
| HEXENYL ISOBUTYRATE CIS-3 10% DPG | 7 |
| HEXENYL SALICYLATE CIS-3 | 22 |
| HEXYL CINNAMIC ALDEHYD ALPHA | 15 |
| INDOL FF 10% DPG | 3 |
| IONONE BETA | 15 |
| ISO E SUPER | 30 |
| JASMONE CIS 10% DPG | 5 |
| CARROT SEED OIL 10% DPG | 2 |
| LEAFOVERT ® | 0.5 |
| LINALOOL | 40 |
| LINALYL ACETATE | 50 |
| MACROLIDE ® SUPRA | 30 |
| MAGNOLAN | 20 |
| MANDARINAL | 1 |
| MANZANATE 1% DPG | 4 |
| METHYL ANTHRANILATE 10% DPG | 1 |
| METHYL HEPTENONE-6,5,2 10% DPG | 1 |
| METHYL NAPHTHYL KETONE BETA 10% DPG | 1.5 |
| MINTONATE | 11 |
| ORANGE OIL | 45 |
| ORYCLON ® SPECIAL | 20 |
| PHENYL ETHYL ALCOHOL | 7 |
| PHENYL ETHYL ISOBUTYRATE | 1.5 |
| PRUNELLA | 5 |
| ROSAPHEN ® | 8 |
| TETRAHYDROLINALOOL | 30 |
| VANILLIN 10% DPG | 1 |
| VERTACETAL ® COEUR | 6 |

With the addition of 2% of a 10% solution of 8,8-dimethyl-6,10-dioxaspiro[4.5]decane (compound of formula (I)), the mixture appears stronger, more floral and more green-fruity.

2. Example: Perfume Oil P2

| | |
|---|---|
| ETHYL ACETOACETATE | 15 |
| AMBROCENIDE ® cryst. 1% DPG | 6 |
| AMBROXIDE | 10 |
| BENZYL ALCOHOL DD | 18 |
| BERGAMOTTE OIL BERGAPTEN FREE | 40 |
| CARDAMOMEN OIL 10% DPG | 10 |
| CEDAR WOOD OIL | 10 |
| CEDRAMBER | 40 |
| LEMON OIL ITAL. | 38 |
| COUMARIN 10% DPG | 5 |
| DAMASCENONE 10% DPG | 5 |
| DAVANA OIL F. PERF. 10% DPG | 7.5 |
| DIMETHYL BENZYL CARBINYL ACETATE 10% DPG | 4.5 |
| DIPROPYLENE GLYCOL | 52 |
| ETHYL HEPTYLATE 10% DPG | 1.5 |
| ETHYL PROPIONATE 10% DPG | 4.5 |
| EVERNYL | 2 |
| FLOROSA | 10 |
| GERANIOL SUPRA | 5 |
| GLOBALIDE ® | 10 |
| GRAPEFRUIT OIL | 20 |
| HEDIONE HC/30 | 50 |
| GINGER OIL 10% DPG | 5 |
| IONONE BETA | 10 |
| ISO E SUPER | 350 |
| JASMAPRUNAT 10% DPG | 10.5 |
| SPEARMINT OIL 65% AMERIC. | 10 |
| LIME OIL COLD PRESSED | 20 |
| LINALOOL | 40 |
| LINALYL ACETATE | 20 |
| BAY LEAVE OIL FLS | 5 |
| MAJANTOL ® | 30 |
| MANDARINE OIL ITAL. | 2 |
| NEROLI ARTESSENCE | 4 |
| ORANGEN BLOSSOM ABS. 10% DPG | 2 |
| ORANGE OIL BITTER | 6 |
| ORANGE OIL ITAL. SWEET ENTF. | 10 |
| PATCHOULI OIL ENTF. DM | 15 |
| PERU BALSAM OIL ED | 1.5 |
| PETITGRAIN OIL PARAG. BOLEADOR | 2 |
| ROSEMARY OIL TUN. | 5 |
| SANDALWOOD OIL EASTINDIAN | 2 |
| SANDRANOL | 2 |
| SULTANENE ® 1% DPG | 1.5 |
| TABANON COEUR | 3 |
| THYME OIL WHITE 1% DPG | 10 |
| TOLU RESIN 10% DPG | 7.5 |
| VERTOFIX | 50 |
| VETIVER OIL HAITI | 5 |
| VERTACTAL COEUR | 2 |
| CINNAMON BARK OIL MADAG. 10% DPG | 5 |

With the addition of 3% 8,8-dimethyl-6,10-dioxaspiro[4.5]decane (compound of formula (I)) the mixture becomes fresher, the fruity notes are enhanced and the compound of formula (I) provides a harmonious, natural note.

3. Example: Perfume Oil P3

| | |
|---|---|
| ALDEHYDE C 8 | 3.5 |
| ALDEHYDE C10 | 6.5 |
| GLYCOLIERRAL | 10 |
| FLOROPAL | 45 |
| RHUBAFURANE | 2.5 |
| STYROLYL ACETATE | 25 |
| ORANGE OIL | 304 |

| | |
|---|---|
| GRAPEFRUIT OIL | 50 |
| GRAPEFRUIT OIL TERPENE | 250 |
| AMAROCIT ® | 45 |
| CORPS 1490 10% DPG | 3.5 |
| ALLYL HEPTYLATE | 3.5 |
| NECTARYL | 5 |
| THIOMENTHANONE-8,3 10% DPG | 6.5 |
| LINALOOL | 95 |
| NEROL 900 | 35 |
| HEDIONE | 100 |

With the addition of 5% 8,8-dimethyl-6,10-dioxaspiro[4.5]decane (compound of formula (I)), the mixture becomes more natural, less sulphurous, more fruity, rounder, fresher and tangier.

4. Example: Perfume Oil P4

| | |
|---|---|
| HEXENOL CIS-3 | 7.5 |
| STEMONE | 10 |
| ORANGE OIL | 75 |
| CORPS 1490 1% DPG | 6 |
| OXANE 10% DPG | 3.5 |
| PINENE BETA NAT. | 120 |
| THIOMENTHANONE-8,3 10% DPG | 3.5 |
| LINALOOL | 95 |
| LINALOOL OXIDE | 3.5 |
| DIMETHYL BENZYL CARBINYL ACETATE | 15 |
| ROSE OXIDE HIGH CIS | 5 |
| PHENYL ETHYL ALCOHOL | 95 |
| CITRONELLOL 950 | 120 |
| HEDIONE | 90 |
| VELOUTONE | 6 |
| ANISYL ACETATE | 20 |
| CINNAMIC ALCOHOL | 5 |
| DIPROPYLENE GLYCOL | 310 |

With the addition of 10% 8,8-dimethyl-6,10-dioxaspiro[4.5]decane (compound of formula (I)), the mixture becomes less sulphurous, more fruity, round, floral and natural.

5. Example: Odour Description of Preferred Fragrance Substances after the Addition of 8,8-dimethyl-6,10-dioxaspiro[4.5]decane (Compound of Formula (I))

| Fragrance substances | Type | Dosage compound of formula (I) | Odour description compared to the odour of the pure fragrance substance |
|---|---|---|---|
| Sultanene (M = 154) | Ester | 1% | more impact, fresher, more natural, more fruity, brighter |
| Aprifloren (M = 184) | Lactone | 0.2% | stronger fruity, juicier |
| Datilat (M = 196) | Ester | 0.4% | more impact and radiance, more fruity, tangier |
| Buccoxim (M = 167) | Oxime | 0.2% | less sulphurous, stronger, more fruity, more natural, more volume |
| Vertacetal Coeur (M = 206) | Acetal | 0.2% | less metallic, rounder, natural, more fruity |
| Oxanthia 50% in TEC (M = 160) | Sulphur compound | 0.7% | less sulphurous, more fruity, more natural |
| Cassiffix (M = 234) | Ether | 0.3% | more impact, more juicy-fruity |
| Isoamyl acetate (M = 130) | Ester | 0.7% | more banana, more juicy-fresh |
| Ethyl Methyl Butyrate-2 (M = 130) | Ester | 0.5% | less metallic, more fruity, more round |
| Fragolane (M = 188) | Ester/Acetal | 0.3% | more strawberry, fresher, more natural |
| Pyroprunat (M = 222) | Ester | 0.5% | more fruity-sweet, more like ripe fruit |
| Cassix 150 (M = 134) | Sulphur compound | 1% | less sulphur note, softer, rounder and more naturalness |
| Allycyclohexyl-propionate (M = 196) | Ester | 0.6% | more impact, fresher and more radiant |
| Allycapronat (M = 156) | Ester | 0.6% | more impact, more aqueous-transparent, fresher |
| Frutinat (M = 170) | Ester | 0.7% | more impact, juicier and fruitier |
| Isopentyrate (M = 170) | Ester | 0.6% | more impact, more radiant, fresher |
| Buccoflor (M = 148) | Schwefel-verbindung | 0.5% | more impact, juicier, fresher and fruitier |
| Thiocineol (M = 170) | Schwefel-verbindung | 1% | less sulphur and onion note, more fruity and juicy |
| Thiomenthanone-8,8 (M = 148) | Schwefel-verbindung | 1% | less sulfur note, more fruity and juicy |

6. Manufacturing Specification of 8,8-dimethyl-6,10-dioxaspiro[4.5]decane (Compound of Formula (I))

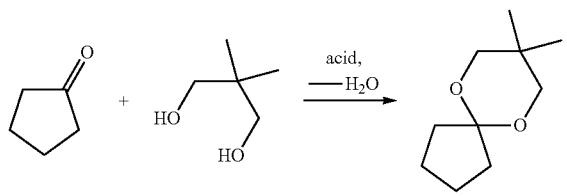

In a 1000 ml three-necked flask with stirrer, contact thermometer, heating mantle, and water separator, 126 g (1.5 mol) cyclopentanone, 156 g (1.5 mol) 2,2-dimethyl-1,3-propanediol, 1.5 g p-toluenesulfonic acid in 305 g cyclohexane are provided and boiled 2-3 at the water separator. After cooling to RT, wash 2× with soda solution and concentrate. The residue is distilled over a 10 cm M.F.K. (boiling range: 72-73° C./10 mbar).

Yield: 219 g (corresponds to 85.9% of theory)

MS: m/z (%)=170 (7), 141(100), 85(34), 69(68), 67(13), 56(43), 55(67), 41(33).

$^1$H-NMR (400 MHz, DMSO-d6) δ 3.39 (s, 4H), 1.82-1.73 (m, 4H), 1.62-1.50 (m, 4H), 0.89 (s, 6H).

Formulation Examples

The perfume oils P1, P2, P3 or P4 from the above perfume oil examples 1 to 4 were each separately incorporated into the following formulations.

The olfactory effects described above under the respective perfume oil were also observed in the following formulations, respectively.

Example F1—Washing Powder

| Material | Chemical name | Function | Weight-% | Weight-% |
|---|---|---|---|---|
| Sodium metasilicate pentahydrate | Sodium Metasilicate Pentahydrate | | Ad 100 | Ad 100 |
| Sodium hydrogen carbonate | Sodium hydrogen carbonate | Alkali | 15.0 | 15.0 |
| Sodium percarbonate | Sodium carbonate peroxyhydrate | Bleach | 15.0 | 15.0 |
| Peractive AC Blue | TAED/Na-Carboxymethylcellulose | Activator | 5.00 | 5.00 |
| Genapol OA-080 | Oxoalcohol C14-15, 8EO | Nonionic surfactant | 3.00 | 3.00 |
| Texapon K12 powder | Sodium Lauryl Sulphate C12 | Anionic surfactant | 7.00 | 7.00 |
| Tinopal CBS-X | | Brightener | 0.50 | 0.50 |
| Savinase 6.0 T, Type W | Protease | Enzyme | 0.40 | 0.40 |
| Termamyl 120 T | Alpha-Amylase | Enzyme | 0.30 | 0.30 |
| Sodium sulphate | Sodium Sulphate | Filler | 5.50 | 5.50 |
| Perfume oil P1, P2, P3 or P4 | | Perfume (Fragrance) | 0.30 | 0.50 |

Example F2—All-Purpose Cleaner

| Material | Chemical name | Function | Weight-% | Weight-% |
|---|---|---|---|---|
| Deionised water | Water | Solvent | Ad 100 | Ad 100 |
| Mergal K9N | 5-Chloro-2-methyl-3-(2H)-isothiazolone and 2-methyl-3-(2H)-isothiazolone | Preservative | 0.1 | 0.1 |
| Trisodium citrate dihydrate | Tri Sodium Citrate Dihydrate | Complexing agent | 3.0 | 3.0 |
| Zetesol NL-2 | Fatty alcohol C12-14-sulphate, Sodium | Anionic Surfactant | 30.0 | 30.0 |
| Imbentin C/125/055 | Fatty alcohol C12-C15, 8EO | Nonionic Surfactant | 5.0 | 5.0 |
| Ethanol | Ethanol | Solvent | 2.0 | 2.0 |
| Perfume oil P1, P2, P3 or P4 | | Perfume (Fragrance) | 0.3 | 0.5 |

Example F3—Shampoo

| Material | INCI-Name | Weight-% | Weight-% |
| --- | --- | --- | --- |
| Deionised water | Water | Ad 100 | Ad 100 |
| Plantacare PS 10 | Sodium Laureth Sulphate, Lauryl Glucoside | 20.0 | 20.0 |
| Euperlan PK 771 | Glycol Distearate, Sodium Lauryl Sulphate, Cocamide MEA, Laureth-10 | 6.0 | 6.0 |
| Dragocid Liquid | Phenoxyethanol, Methylparaben, Ethylparaben, Butylparaben, Propylparaben, Isobutylparaben | 0.5 | 0.5 |
| Sodium chloride | Sodium Chloride | 1.4 | 1.4 |
| Citric acid monohydrate crystalline | Citric Acid | 0.1 | 0.1 |
| Perfume oil P1, P2, P3 or P4 | Perfume (Fragrance) | 0.5 | 0.8 |

Example F4—Shower Gel

| Material | INCI-Name | Weight-% | Weight-% |
| --- | --- | --- | --- |
| Deionised water | Water | Ad 100 | Ad 100 |
| Plantacare PS 10 | Sodium Laureth Sulphate, Lauryl Glucoside | 20.0 | 20.0 |
| Dragocid liquid | Phenoxyethanol, Methylparaben, Ethylparaben, Butylparaben, Propylparaben, Isobutylparaben | 0.5 | 0.5 |
| Sodium chloride | Sodium Chloride | 1.4 | 1.4 |
| Citric acid monohydrate crystalline | Citric Acid | 1.3 | 1.3 |
| Perfume oil P1, P2, P3 or P4 | Perfume (Fragrance) | 0.5 | 0.7 |

Example F5—Fabric Softener

| Material | Chemical name | Function | Weight-% | Weight-% |
| --- | --- | --- | --- | --- |
| Deionised water | Water | Solvent | Ad 100 | Ad 100 |
| Rewoquat WE 18 | Dialkylesterammonium-ethosulphate | Cationic Surfactant | 16.6 | 16.6 |
| Mergal K9N | 5-Chloro-2-methyl-3-(2H)-isothiazolone und 2-methyl-3-(2H)-isothiazolone | Preservative | 0.10 | 0.10 |
| Dow Corning 1520 Antifoam | Polydimethyl-siloxane | Defoamer | 0.30 | 0.30 |
| Magnesium chloride 1% solution | Magnesium Chloride Solution | Consistency Enhancer | 10.00 | 10.00 |
| Perfume oil P1, P2, P3 or P4 | | Fragrance | 0.55 | 0.75 |

Example F6—Eau De Cologne/Eau De Toilette

| Ingredients | Weight-% | Weight-% |
| --- | --- | --- |
| Perfume oil P1, P2, P3 or P4 | 5 | 10 |
| Ethanol | Ad 100 | Ad 100 |
| Water | 18 | 10 |

Example F7—Aerosol-Pumpspray

| Ingredients | Weight-% | Weight-% |
| --- | --- | --- |
| Perfume oil P1, P2, P3 or P4 | 1.0 | 1.5 |
| Ethanol | Ad 100 | Ad 100 |
| Water | 5.0 | 8.0 |
| Alpha-Tocopherol | 0.20 | 0.20 |
| Hydroxypropyl cellulose | 0.20 | — |
| Rosemary extract, soluble in ethanol | 0.22 | — |
| Cetyl alcohol | 1.00 | 0.50 |

Example F8—Shampoo

| Ingredients | Weight-% | Weight-% | Weight-% |
| --- | --- | --- | --- |
| Sodium lauryl ether sulphate (e.g. Texapon NSO, Company Cognis Deutschland GmbH) | 12 | 12 | 12 |
| Cocamidopropyl betaine (e.g. Dehyton K, Company Cognis Deutschland GmbH) | 2 | 2 | 2 |
| Sodium chloride | 1.4 | 1.4 | 1.4 |
| Citric acid | 1.3 | 1.3 | 1.3 |
| Phenoxyethanol, Methyl-, Ethyl-, Butyl- and Propyl paraben | 0.5 | 0.5 | 0.5 |
| Perfume oil P1, P2, P3 or P4 | 0.3 | 0.5 | 0.7 |
| Water | Ad 100 | Ad 100 | Ad 100 |

Example F9—Washing Powder

| Ingredients | Weight-% | Weight-% | Weight-% |
|---|---|---|---|
| Linear Na-alkyl benzene sulphonate | 8.8 | 8.8 | 8.8 |
| Ethoxylated fatty alcohol C12-18 (7 EO) | 4.7 | 4.7 | 4.7 |
| Na soap | 3.2 | 3.2 | 3.2 |
| Defoamer DOW CORNING(R) 2-4248S POWDERED ANTIFOAM, silicone oil on zeolite as carrier material | 3.9 | 3.9 | 3.9 |
| Zeolite 4A | Ad 100 | Ad 100 | Ad 100 |
| Na carbonate | 11.6 | 11.6 | 11.6 |
| Na salt of a copolymer of acrylic and maleic acid (Sokalan CP5) | 2.4 | 2.4 | 2.4 |
| Na silicate | 3.0 | 3.0 | 3.0 |
| Carboxymethyl cellulose | 1.2 | 1.2 | 1.2 |
| Dequest 2066([[(Phosphono-methyl)imino]bis[(ethylene-nitrilo)bis(methylene)]]tetrakis-phosphonic acid, sodium salt) | 2.8 | 2.8 | 2.8 |
| Optical brightener | 0.2 | 0.2 | 0.2 |
| Na sulphate | 6.5 | 6.5 | 6.5 |
| Protease | 0.4 | 0.4 | 0.4 |
| Sodium perborate tetrahydrate | 21.7 | 21.7 | 21.7 |
| Perfume oil P1, P2, P3 or P4 | 0.25 | 0.35 | 0.5 |
| EDTA | 1.0 | 1.0 | 1.0 |

Example F10—Liquid Detergent

| Ingredients | Weight-% |
|---|---|
| Deionised water | 39.9 |
| Optical brightener | 0.10 |
| Coconut fatty acids (C12-C18) | 7.5 |
| Potassium hydroxide 50% solution | 4.3 |
| Propane-1,2-diol | 5.00 |
| Fatty alcohols C12-C15, 8 EO | 12.0 |
| Na salt of secondary alkyl sulphonates (C13-C17) | 17.0 |
| Triethanolamine | 2.0 |
| Trisodium citrate dihydrate | 5.0 |
| Dequest 2066([[(Phosphono-methyl)imino]bis[(ethylene-nitrilo)bis(methylene)]]tetrakis-phosphonic acid, sodium salt) | 3.0 |
| Ethanol | 3.0 |
| Enzymes | 0.7 |
| Perfume oil P1, P2, P3 or P4 | 0.5 |

Example F11—Liquid Detergent Concentrate

| Ingredients | Weight-% |
|---|---|
| Deionised water | 13.4 |
| Coconut fatty acids (C12-C18) | 10.0 |
| Fatty alcohols C12-C15, 8 EO | 26.0 |
| Na salt of secondary alkyl sulphonates (C13-C17) | 26.5 |
| Triethanolamine | 8.5 |
| Na salt of fatty alcohol sulphates C12-C14 | 3.0 |
| Ethanol | 5.5 |
| Urea | 4.5 |
| Enzymes | 0.9 |
| Citric acid | 1.0 |
| Perfume oil P1, P2, P3 or P4 | 0.7 |

The invention claimed is:

1. A fragrance substance mixture comprising:
    (a) a compound of formula (I)

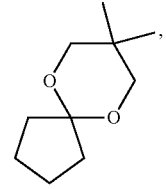

and
    (b) one or more fragrance substance(s) with a fruity olfactory note selected from the group consisting of esters, lactones, oximes and sulphur compounds with a molar mass of 240 g/mol or less, and/or
    (c) one or more fragrance substance(s) selected from the group consisting of acetals, ketones, and ethers, with a molar mass in the range of 126-240 g/mol.

2. The fragrance substance mixture according to claim 1, wherein component (b) comprises two or more different fragrance substances, and/or component (c) comprises two or more different fragrance substances.

3. The fragrance substance mixture according to claim 1, wherein the mass ratio of the total amount of fragrance substance(s) of component (b), if present, to the compound of formula (I) is greater than or equal to 40:60, and/or
    the mass ratio of the total amount of fragrance substance(s) of component (c), if present, to the compound of formula (I) is greater than or equal to 60:40.

4. The fragrance substance mixture according to claim 1 comprising the one or more fragrance substance(s) of component (b), wherein the one or more fragrance substance(s) of component (b) has/have a molar mass in the range of 130 to 240 g/mol.

5. The fragrance substance mixture according to claim 1, wherein the one or more fragrance substance(s) of component (b), if present, is/are selected are selected from the group consisting of allyl capronate, allylcyclohexyl propionate, 5-hexyl-4-methyl-tetrahydrofuran-2-one, ethyl-2-cyclopent-2-en-1-yl acetate, 1-cyclohexylethyl-(E/Z)-but-2-enoate, 1,5-dimethylbicyclo[3.2.1]octan-8-one oxime, 2,4,6-trimethyl-4-phenyl-1,3-dioxane, 2-methyl-4-propyl-1,3-oxathiane, isopentyl acetate, ethyl-2-(2,4-dimethyl-1,3-dioxolan-2-yl)acetate, ethyl-2-methylbutanoate, (2-cyclopentylcyclopentyl)-(E/Z) -but-2-enoate, 4-methoxy-2-methyl-butane-2-thiol, 1,3-dimethylbutyl-(E/Z) -but-2-enoate, 1,3-dimethylbut-3-enyl-2-methylpropanoate, 1-methoxyhexane-3-thiol, 4-isopropyl-1-methyl-7-thiabicyclo[2.2.1]heptane, 2-(4-methylcyclohex-3-en-1-yl) propane-2-thiol, 5-methyl-2-(1-methyl-1-sulfanyl-ethyl) cyclohexanone, (1,3-dimethyl-3-phenyl-butyl)acetate, allyl-2-isopentyloxyacetate, 5-butyltetrahydrofuran-2-one, 5-pentyltetrahydrofuran-2-one, 5-heptyltetrahydrofuran-2-one, 5-octyltetrahydrofuran-2-one, 5-hexyltetrahydrofuran-2-one, ethyl-2-(2-methyl-1,3-dioxolan-2-yl)acetate and diethylcyclohexan-1,4-dicarboxylate, and/or the one or more fragrance substance(s) of component (c), if present, is/are selected are selected from the group consisting of 1-(2,6,6-trimethylcyclohex-2-en-1-yl) hepta-1,6-dien-3-one, 1-(2,6,6-trimethylcyclohex-2-en-1-yl)but-2-en-1-one, 1-(2,6,6-trimethylcyclohexen-1-yl)but-2-en-1-one, 1-(2,6,6-trimethylcyclohex-3-en-1-yl)but-2-en-1-one, 1-(2,4,4-trimethylcyclohex-2-en-1-yl)but-2-en-1-one, 1-methyl-4-(2,2,3-trimethylcyclopent-3-en-1-yl)-2-oxabicyclo[2.2.2] octane, 4-(4-methoxyphenyl)-butan-2-one, 5-methylhept-2-en-4-one, 6,6-dimethoxy-2,5,5-trimethyl-hex-2-ene and 2,4,6-trimethyl-4-phenyl-1,3-dioxane.

6. A method for producing the fragrance substance mixture according to claim 1 comprising:
mixing component (a) with component (b) and/or (c).

7. The method according to claim 6, resulting in a fragrance substance mixture in which
the mass ratio of the total amount of fragrance substance (s) of component (b), if present, to the compound of formula (I) is greater than or equal to 40:60, and/or
the mass ratio of the total amount of fragrance substance (s) of component (c), if present, to the compound of formula (I) is greater than or equal to 60:40.

8. A perfumed product comprising a fragrance substance mixture according to claim 1 in a sensorially effective amount.

9. The perfumed product according to claim 8, wherein the product is selected from the group consisting of perfume extracts, eau de parfums, eau de toilettes, aftershaves, eau de colognes, pre-shave products, splash colognes, perfumed refreshing cloths, acidic, alkaline and neutral detergents, textile fresheners, ironing aids, liquid detergents, powdered detergents, laundry pre-treatment agents, fabric softeners, washing soaps, washing tablets, disinfectants, surface disinfectants, air fresheners, aerosol sprays, waxes and polishes, personal care products, hand creams and lotions, foot creams and lotions, depilatory creams and lotions, aftershave creams and lotions, tanning creams and lotions, hair care products, deodorants and antiperspirants, decorative cosmetic products, candles, lamp oils, incense sticks, insecticides, repellents, and fuels,
wherein the perfumed product comprises 0.01 to 10% by weight of the fragrance substance mixture, based on the total mass of the perfumed product.

10. A method for producing a perfumed product comprising:
i) providing a fragrance substance mixture according to claim 1,
ii) providing further components of the perfumed product, and
iii) contacting the further components of the perfumed product provided in ii) with a sensorially effective amount of the fragrance substance mixture provided in i).

11. The fragrance substance mixture according to claim 1, wherein the mass ratio of the total amount of fragrance substance(s) of component (b), if present, to the compound of formula (I) is greater than or equal to 80:20, and/or the mass ratio of the total amount of fragrance substance(s) of component (c), if present, to the compound of formula (I) is greater than or equal 80:20.

12. The fragrance substance mixture according to claim 1, wherein the mass ratio of the total amount of fragrance substance(s) of component (b), if present, to the compound of formula (I) is greater than or equal to 99:1, and/or the mass ratio of the total amount of fragrance substance(s) of component (c), if present, to the compound of formula (I) is greater than or equal 99:1.

13. The fragrance substance mixture according to claim 1 comprising the one or more fragrance substance(s) of component (b), wherein the one or more fragrance substance(s) of component (b) has/have a molar mass in the range of 130 to 240 g/mol.

14. A method for enhancing natural freshness and/or radiance and/or for masking or reducing sulphurous, artificial and/or metallic notes of one or more fragrance substances different from the compound of formula (I)

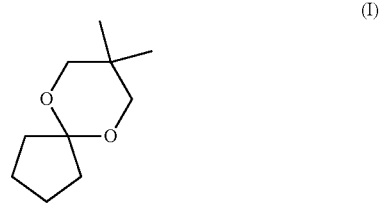

comprising mixing the one or more fragrance substances different from the compound of formula (I) with an amount of the compound of formula (I) sufficient to enhance the natural freshness and/or radiance of the fragrance substances different from the compound of formula (I) and/or to mask or reduce sulphurous, artificial and/or metallic notes of the fragrance substances different from the compound of formula (I), wherein the one or more fragrance substance(s) different from the compound of formula (I) is/are selected from:.
(b) one or more fragrance substance(s) with a fruity olfactory note selected from the group consisting of esters, lactones, oximes and sulphur compounds with a molar mass of 240 g/mol or less, and/or
(c) one or more fragrance substance(s) selected from the group consisting of acetals, ketones, and ethers, with a molar mass in the range of 126-240 g/mol.

15. The method according to claim 14, wherein
the mass ratio of the total amount of fragrance substance(s) of component (b), if present, to the compound of formula (I) is greater than or equal to 40:60, and/or the mass ratio of the total amount of fragrance substance(s) of component (c), if present, to the compound of formula (I) is greater than or equal to 60:40.

16. A fragrance substance mixture comprising:
(a) a compound of formula (I)

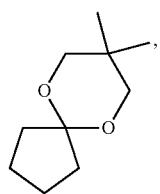

(I)

and
(b) one or more fragrance substance(s) with a fruity olfactory note chosen from esters, lactones, oximes and sulphur compounds with a molar mass of 240 g/mol or less,
wherein the mass ratio of the total amount of fragrance substance(s) of component (b), if present, to the compound of formula (I) is greater than or equal to 80:20, and
the compound of formula (I) enhances the natural freshness and/or radiance of the one or more fragrance substance(s) of (b) and/or masks or reduces sulphurous, artificial and/or metallic notes of the one or more fragrance substance(s) of (b).

17. The fragrance substance mixture according to claim 16, wherein the one or more fragrance substance(s) of component (b) is/are selected are selected from the group consisting of allyl capronate, allylcyclohexyl propionate, 5-hexyl-4-methyl-tetrahydrofuran-2-one, ethyl-2-cyclopent-2-en-1-yl acetate, 1-cyclohexylethyl-(E/Z)-but-2-enoate, 1,5-dimethylbicyclo[3.2.1]octan-8-one oxime, 2,4,6-trimethyl-4-phenyl-1,3-dioxane, 2-methyl-4-propyl-1,3-oxathiane, isopentyl acetate, ethyl-2-(2,4-dimethyl-1,3-dioxolan-2-yl)acetate, ethyl-2-methylbutanoate, (2-cyclopentylcyclopentyl)-(E/Z)-but-2-enoate, 4-methoxy-2-methyl-butane-2-thiol, 1,3-dimethylbutyl-(E/Z)-but-2-enoate, 1,3-dimethylbut-3-enyl-2-methylpropanoate, 1-methoxyhexane-3-thiol, 4-isopropyl-1-methyl-7-thiabicyclo[2.2.1]heptane, 2-(4-methylcyclohex-3-en-1-yl)propane-2-thiol, 5-methyl-2-(1-methyl-1-sulfanyl-ethyl)cyclohexanone, (1,3-dimethyl-3-phenyl-butyl)acetate, allyl-2-isopentyloxyacetate, 5-butyltetrahydrofuran-2-one, 5-pentyltetrahydrofuran-2-one, 5-heptyltetrahydrofuran-2-one, 5-octyltetrahydrofuran-2-one, 5-hexyltetrahydrofuran-2-one, ethyl-2-(2-methyl-1,3-dioxolan-2-yl)acetate and diethylcyclohexan-1,4-dicarboxylate.

18. The fragrance substance mixture according to claim 16, wherein the mass ratio of the total amount of fragrance substance(s) of component (b) to the compound of formula (I) is greater than or equal to 99:1.

* * * * *